United States Patent [19]
Norcross, Jr.

[11] Patent Number: 5,959,196
[45] Date of Patent: Sep. 28, 1999

[54] IN-LINE VISCOMETER

[75] Inventor: Robert Norcross, Jr., Newton, Mass.

[73] Assignee: Norcross Corporation, Newton, Mass.

[21] Appl. No.: 08/900,170

[22] Filed: Jul. 25, 1997

Related U.S. Application Data

[60] Provisional application No. 60/024,787, Sep. 10, 1996.

[51] Int. Cl.$^6$ .................................................. G01N 11/00
[52] U.S. Cl. ............................................................ 73/54.18
[58] Field of Search ................................ 73/54.15, 54.16, 73/54.18, 54.21, 54.01

[56] References Cited

U.S. PATENT DOCUMENTS

| | | | |
|---|---|---|---|
| 2,491,389 | 12/1949 | Norcross | 73/54.16 |
| 3,304,765 | 2/1967 | Norcross | 73/57 |
| 3,512,396 | 5/1970 | Okamoto | 73/54.16 |
| 3,677,070 | 7/1972 | Norcross | 73/57 |
| 3,686,931 | 8/1972 | Norcross | 73/57 |
| 3,717,026 | 2/1973 | Ito | 73/57 |
| 3,782,174 | 1/1974 | Varadi et al. | 73/54.16 |
| 4,154,094 | 5/1979 | Norcross | 73/57 |
| 4,627,272 | 12/1986 | Wright | 73/57 |
| 4,864,849 | 9/1989 | Wright | 73/57 |
| 5,327,778 | 7/1994 | Park | 73/54 |
| 5,388,447 | 2/1995 | Fitch et al. | 73/54 |
| 5,569,843 | 10/1996 | Poissant | 73/54 |

*Primary Examiner*—Hezron Williams
*Assistant Examiner*—Jay L. Politzer
*Attorney, Agent, or Firm*—Ernest V. Linek; Dike, Bronstein, Roberts & Cushman, LLP

[57] ABSTRACT

The viscometer of the present invention comprises a chamber, and inside the chamber is secured a measuring tube and a falling piston. The piston has a lift plate secured to its top by means of a short small shaft. There are one or more lifting fingers, which operate through a defined distance large enough to raise the piston up and then drop back down to a base position thus leaving the piston free to fall by gravity to its lowermost position. However, the mechanical design is such that these fingers when lowered will not touch the actual piston itself. Mounted underneath the piston, when it is in its lowermost position, is a proximity switch that is used to sense when the piston is in its lowermost position. The time it takes to travel from its raised position to its lowermost position is a function of viscosity. The present invention combines the concept of a "falling member" with a compact bi-directional flow concept and an easily opened and cleaned measuring chamber. It is also very compact in size and does not require a specific flow of fluid to operate.

20 Claims, 8 Drawing Sheets

IN-LINE VISCOMETER

BACKGROUND OF THE INVENTION

This is a provisional application Ser. No. 60/024,787, filed Sep. 10, 1996.

In the world of process viscosity control there are a number of locations where viscosity can be measured: in a tank, a reactor or in-line (e.g., in a pipeline). There are devices available for measuring in all of these locations. Each device has certain advantages and disadvantages.

Various instruments for controlling viscosity and consistency include viscometers such as the Saybolt, which are based on timed discharge through nozzle that is commonly used for expressing viscosities of oils. Timed fall of a ball or rise of a bubble is employed in a typical laboratory method for measuring oil viscosity. A continuous viscosity meter, such as the Fischer and Porter Company instrument, is based on a gear pump diverting a portion of product stream through a flow bridge where a pressure differential between two reference points is established. The differential pressure is a measure of the viscosity of the material.

Another type viscometer by Norcross Corporation employs a piston that is raised in a time sequence and falls by gravity through a liquid. Time of fall is recorded as a measure of viscosity. A torque to rotate a cylindrical element in a liquid is the principle employed in the Brookfield Engineering Company viscometer. In this viscometer a synchronous motor drives a vertical spindle with disk, paddle or cylinder submerged in a test liquid. Drive is through a calibrated spring. Angular lag of spindle behind motor is proportional to viscosity and is measured in various ways.

Many of these viscometers are patented. See for example the following U.S. Pat. Nos. 4,154,094, 3,686,931, 3,677,070 and 3,304,765, the contents of which are hereby incorporated herein by reference. See Also U.S. Pat. No. 3,717,026.

A viscosity-sensitive rotameter by Fischer and Porter Company employs rotameter bobs which are designed for either sensitivity or immunity to viscosity. With constant flow rate a sensitive bob can be calibrated for viscosity. One method is to use an immune bob to set flow at a series of index marks to measure viscosity by reference to the calibrated scale. Cambridge Applied Systems use a small plunger inside a solenoid coil. See U.S. Pat. No. 4,627,272.

The present invention relates to measuring viscosity "in-line" and has been developed in response to some trends being seen in the measuring of some printing inks, lacquers and other coatings of low viscosity, although this invention could likewise be used on high viscosity materials. There are available several types of in-line viscometers for measuring fluids such as printing inks. These are generally discussed below as Types 1, 2, 3 and 4:

Type 1 utilizes a rolling ball that consists of a ball in a glass tube thorough which the fluid flows. The fluid flow is allowed to pass and the ball is pushed up the tube. The flow is then stopped and the time it takes the ball to roll down the tube is measured, providing a measure of viscosity of the fluid. The tube is maintained at an angle of approximately 45 degrees.

Type 2 utilizes a falling dart that consists of a small "falling dart" in a vertical glass tube. Fluid flow is allowed to pass upward through the tube, thus raising the dart, then the flow is stopped and the dart falls by gravity. The time of fall can be measured with proximity switches, providing a measure of viscosity of the fluid. There are some variations of this type, using different shaped "darts" but the principle remains the same, using fluid flow to lift the falling member.

Type 3 utilizes a falling piston whose position is changed by means of a "push rod" through a Teflon packing holder. The piston is contained within a short pipe that is open at the top and filled in the bottom with the packing holder. An external air cylinder can be used to push a rod through the packing, thus lifting up the piston and drawing a sample of fluid into the space formed beneath the piston. The rod is then withdrawn and the piston falls through the fluid sample and its position is measured by means of a magnetically operated switch mounted external to the fluid. Inside the piston is a magnet that triggers the switch. The time of the piston fall provides a measure of the viscosity of the fluid.

Type 4 is directed to a number of in-line devices using rotational principles of measurement. The viscous drag of the fluid on the rotation of the plate can be measured by means of speed changes, through stuffing boxes and or by means of torsion tubes, providing a measure of the viscosity of the fluid.

All four of these prior art concepts have drawbacks that this new invention overcomes, including the following:

Type 1 and Type 2: These require a finely filtered ink supply and a side stream of ink as well as valves to control the flow of ink. The valves have problems reliably sealing and some processes do not want to have separate piping to create the side stream of flow. These also require flow to be in one direction through their unit. Finally, these units are typically very difficult to open for cleaning and maintenance.

Type 3: This does not require a sidestream, it can go directly in the pipeline and less filtration is required, however the linear operation of a push rod through a packing holder has a definite life expectancy due to the scoring of the Teflon when particles of ink are pulled into the packing, due to linear motion of the push rod. This design also results in a rather large and cumbersome unit with some costly machining components. The manufacturer specifies the direction of fluid flow through this unit. This unit is also difficult to open for cleaning and maintenance. The pressure on the packing is important because loose particles will easily be drawn into the packing and if too many particles are drawn in, the operation of the push rod may be restrained.

Type 4: This principle of operation suffers from a lack of sensitivity and ease of maintenance. As with the Type 3 units, flow direction though this unit is specified by the manufacturer. These units can be removed from pipelines but their "measuring areas" are very difficult to access for cleaning and maintenance. They also suffer from the effect of wear and clogging of their rotational seals, as these seals must have a known resistance in order to properly calibrate the units.

SUMMARY OF THE INVENTION

The present invention provides an in-line viscometer, designed to be connected to the main flow stream, either directly (i.e., in-line) or by means of a bypass connection. Preferably, this invention would be connected directly in the main flow line; but there may be circumstances where having it connected in a bypass line will be preferred. For instance, use of a bypass connection may be advantageous when the unit is employed with a very large main line or for maintenance reasons. If someone does not have a way to flush their lines with solvent between runs, they would preferably place the viscometer in a bypass line, so that they can at least have solvent flow through the unit during runs.

As discussed in greater detail below, the skilled artisan will appreciate the number of ways in which this invention is unique from Types 1, 2, 3 and 4 discussed above. The viscometer of the present invention comprises the following components:

(a) a sealed chamber having bidirectional fluid inlets and outlets;

(b) a measuring tube and a falling piston mounted inside said sealed chamber, wherein the piston has a lift plate secured to its top by means of a shaft;

(c) one or more lifting fingers in contact with said piston that lift the piston to a predetermined uppermost position, and then pull down and out of the way, leaving said piston free to fall by gravity to a predetermined lowermost position; and (d) a proximity switch mounted underneath the piston at its lowermost position, said proximity switch used to sense when the piston is in its lowermost position;

whereby the measured time taken for the piston to travel from its uppermost position to its lowermost position is a direct function of the viscosity of the liquid in the chamber.

BRIEF DESCRIPTION OF THE DRAWINGS

FIGS. 2A, 2B, 2C, 2D, 2F and 2G, respectively illustrate three sectional views of FIG. 1B, taken along line A—A, wherein the piston is in the raised position (2A); the lifting arms have been lowered such that the piston is free to fall (2B); and the piston is in its lowermost position, with the lifting arm ready to raise the piston for the next viscosity reading (2C).

DETAILED DESCRIPTION OF THE INVENTION

Figure 1A:
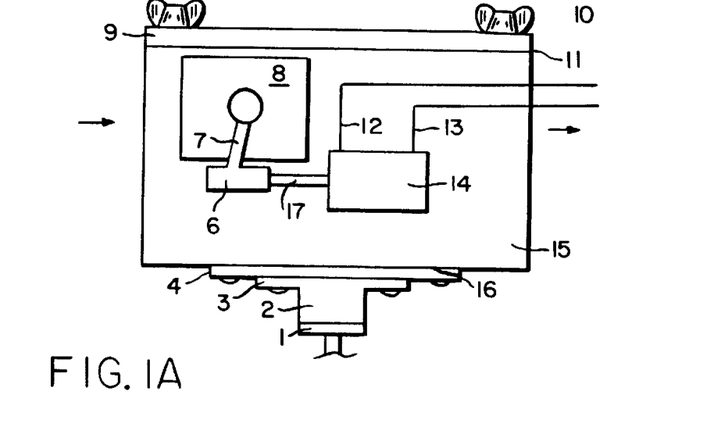
FIGS. 1A, 1B and 1C respectively illustrate a front view, top view and left end view of the preferred embodiment of the viscometer of the present invention.
Figure 1B:
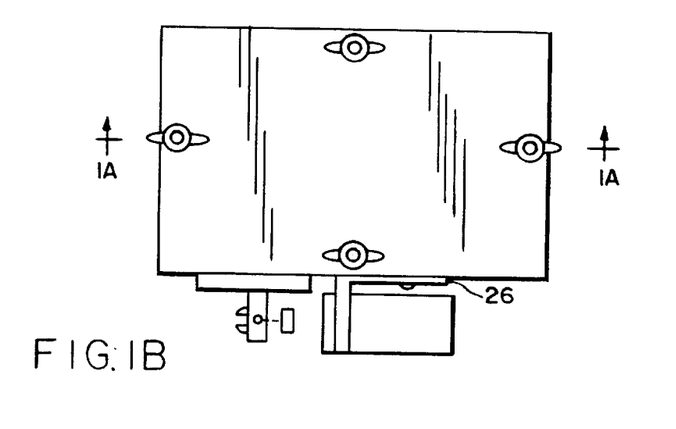
Figure 1C:
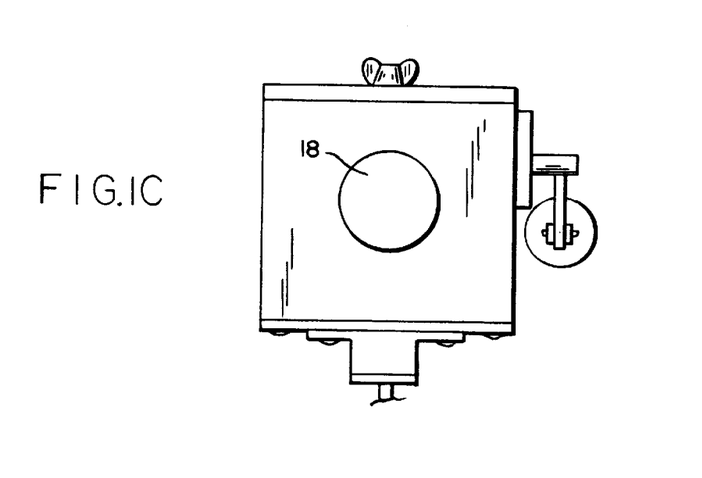
Figure 2A:
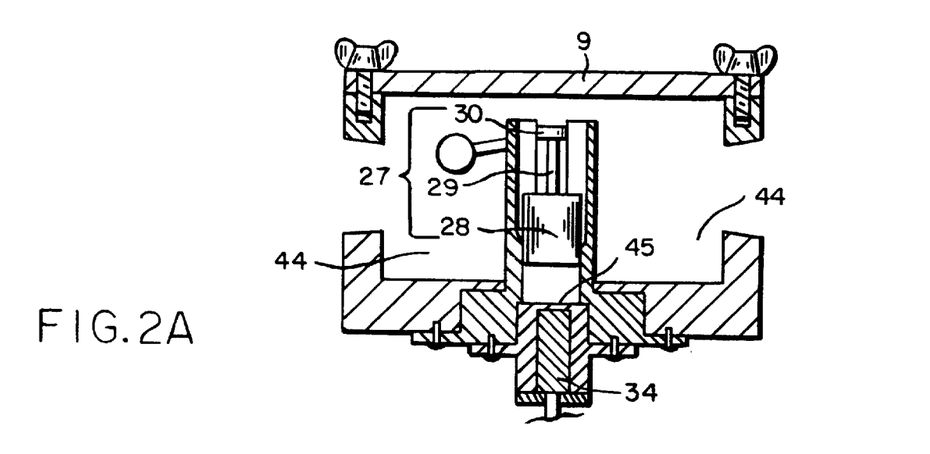
Figure 2B:
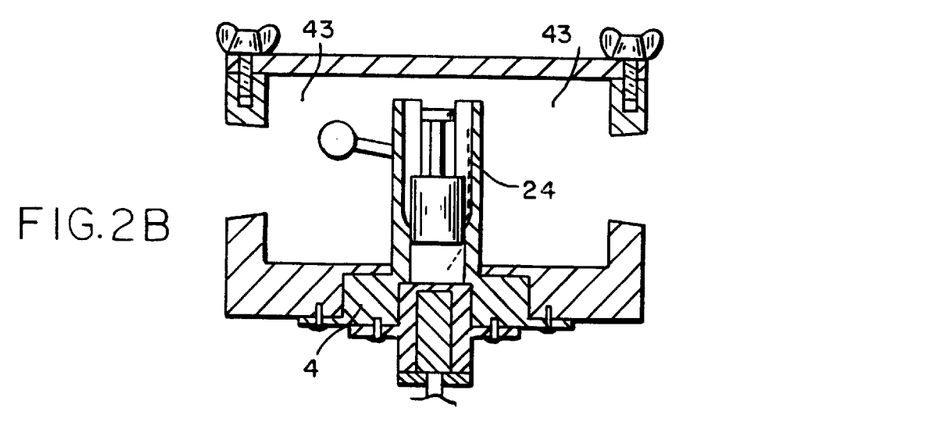
Figure 2C:
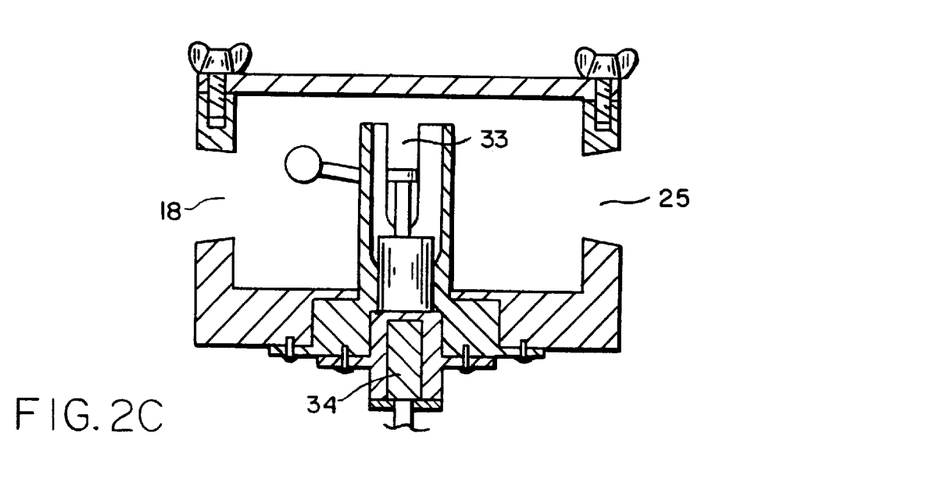
Figure 2D:
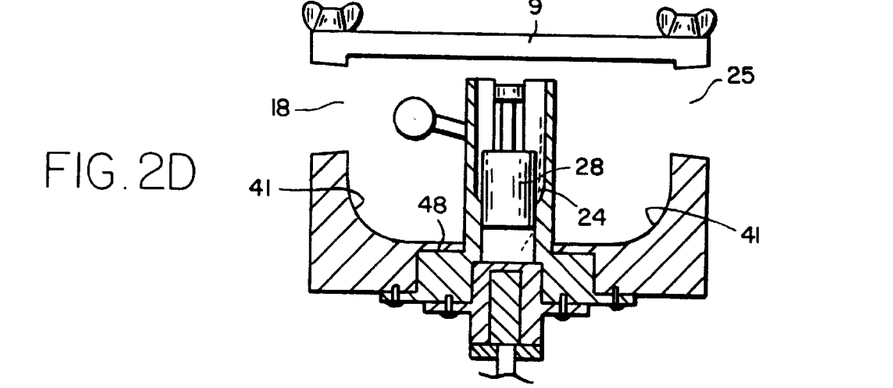
FIGS. 2D, 2E, 2F and 2G, provide close-up details of various components from the sectional view taken along section line A—A.
Figure 2E:
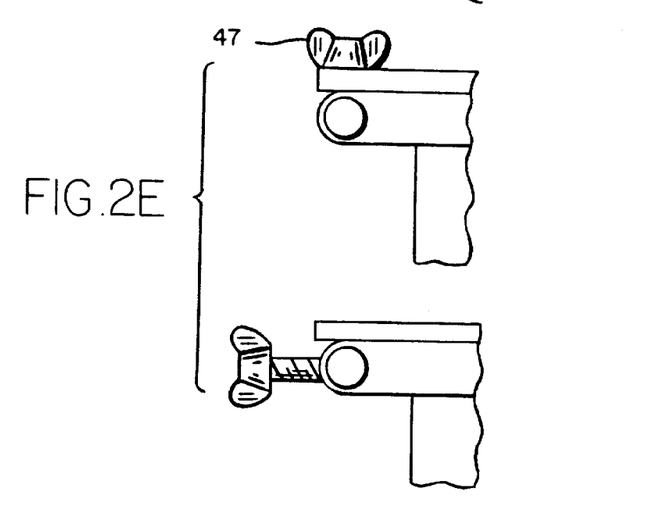
Figure 2F:
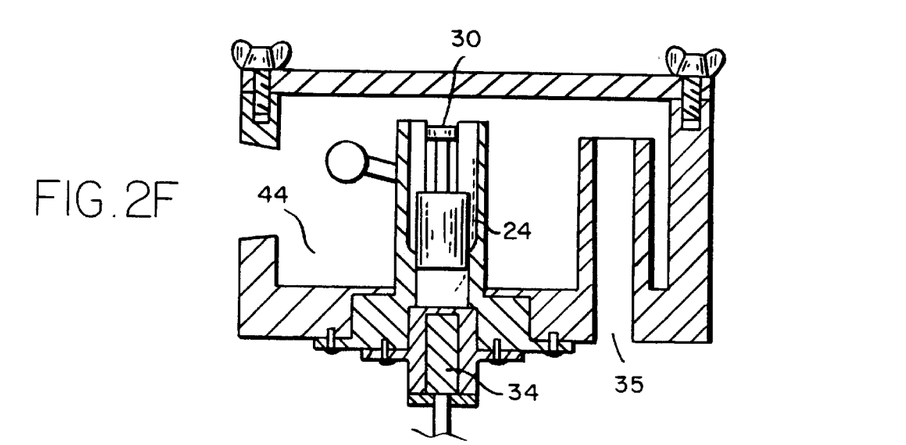
Figure 2G:
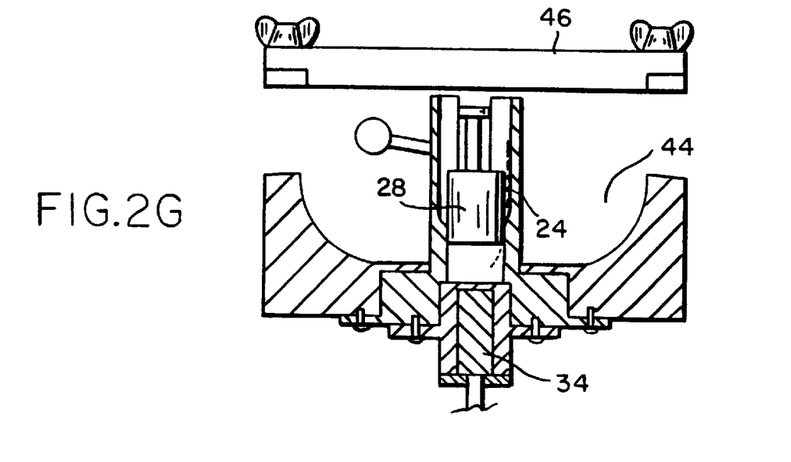
Figure 2H:
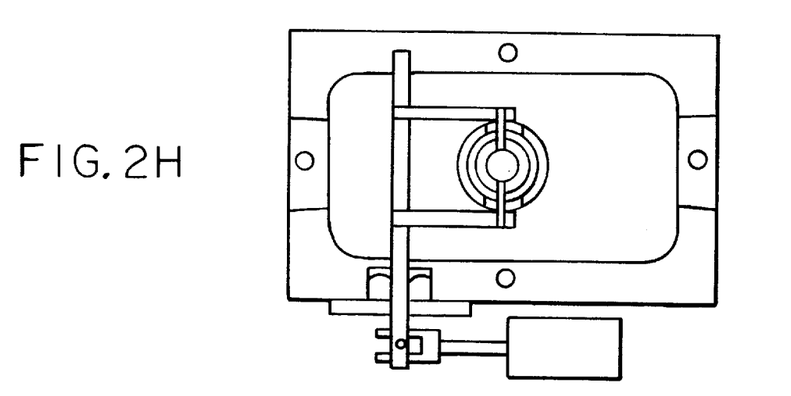
FIGS. 2H and 2I provide close-up details of various component parts illustrated in this sectional view and in the sectional view taken from FIG. 1A along section line B—B.
Figure 2I:
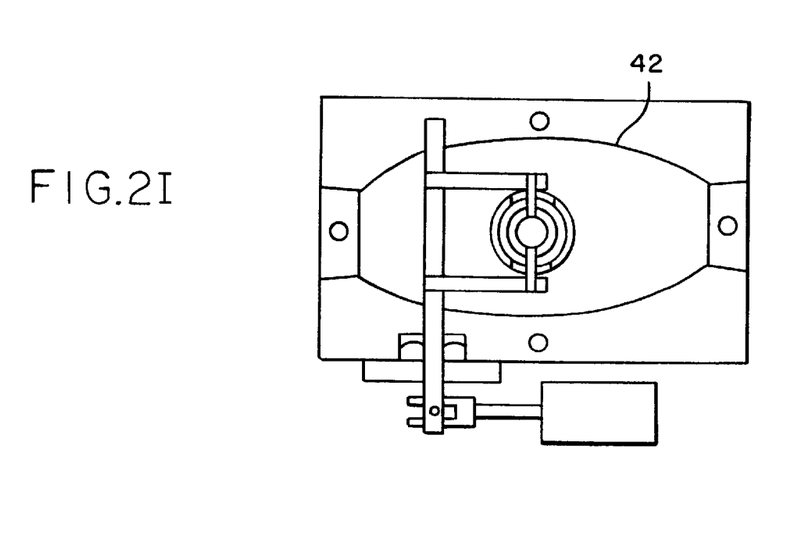
Figure 3A:
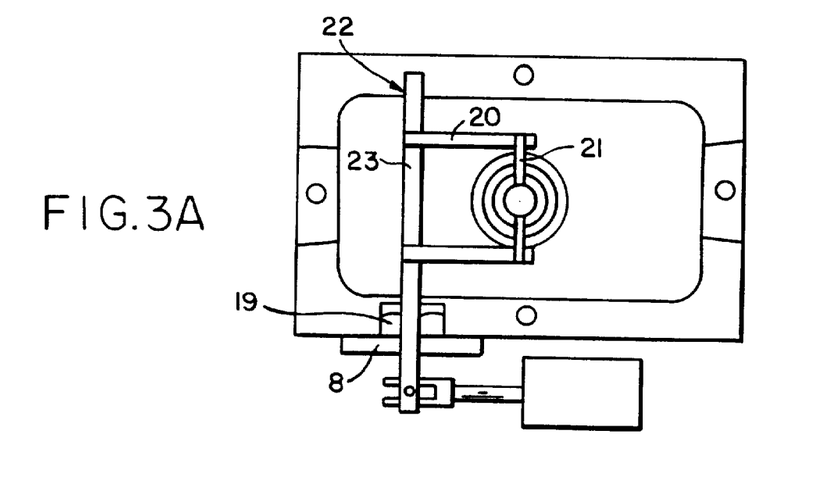
FIGS. 3A, 3B, 3D and 3E illustrate various component parts of the viscometer of the present invention.
Figure 3B:
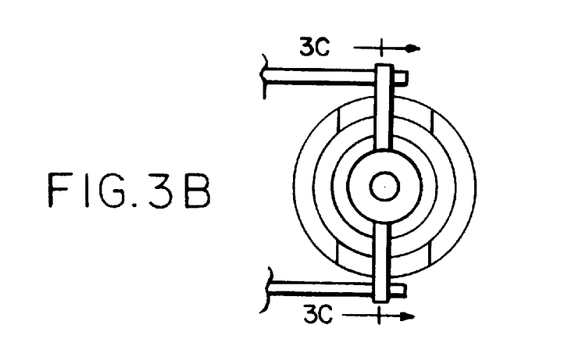
Figure 3C:
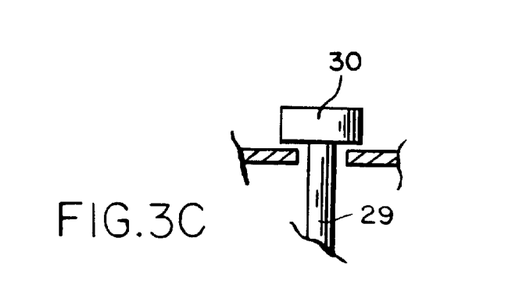
FIGS. 3C and 3F provide close-up details as seen through the sectional view provided by section line C—C of FIG. 1A.
Figure 3D:
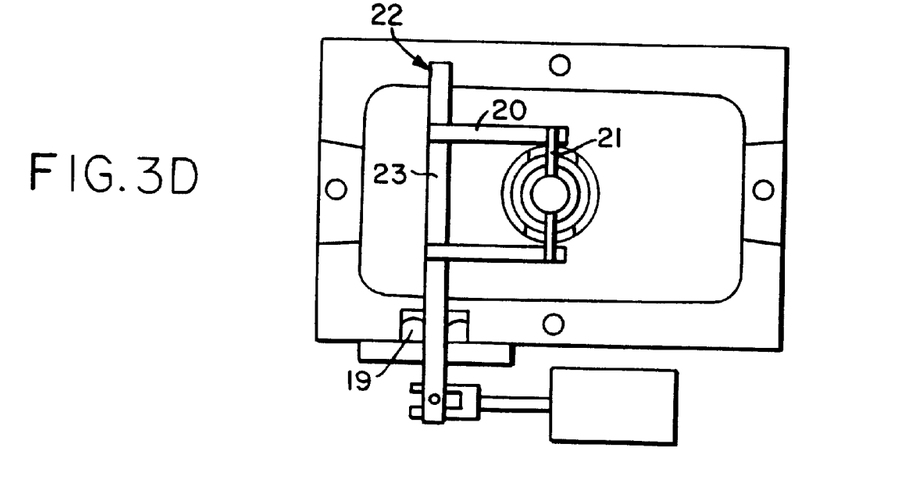
Figure 3E:
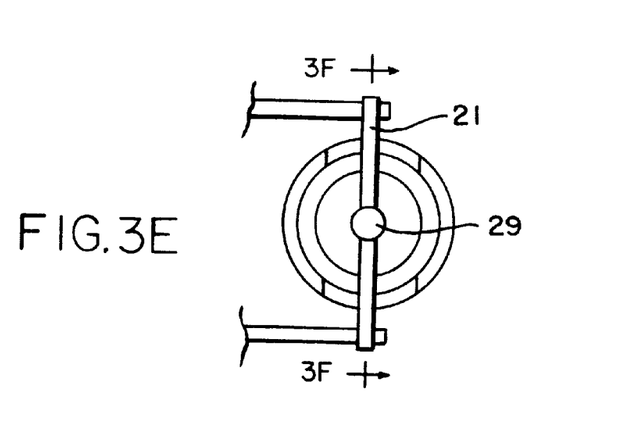
Figure 3F:
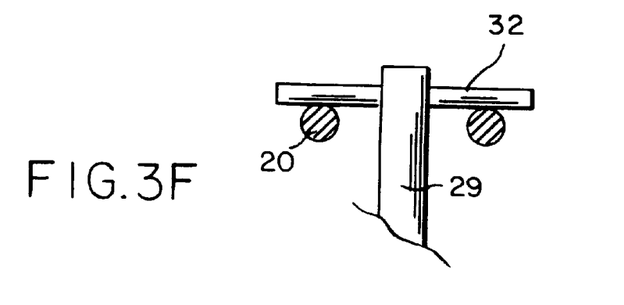
Figure 4A:
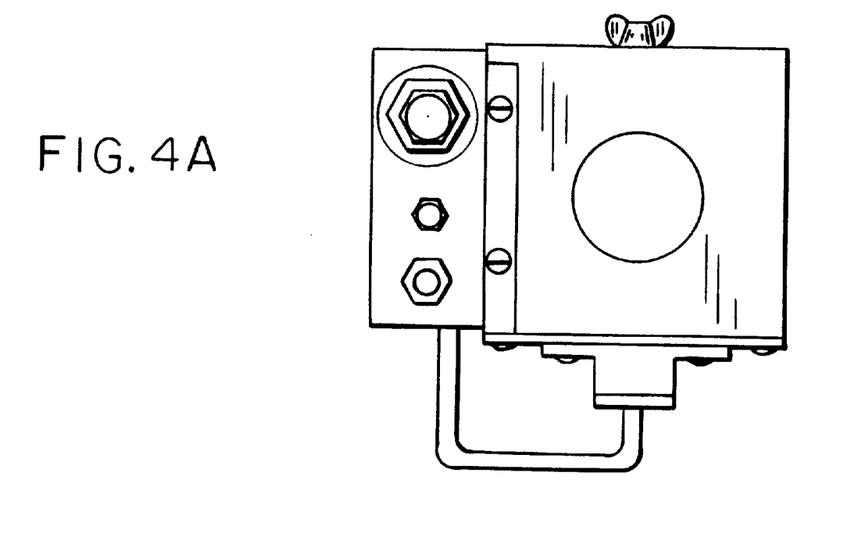
FIGS. 4A, 4B, 4C and 4D respectively illustrate the following outside views of the preferred embodiment of the viscometer of the present invention; right end view (4A), front view (4B), top view (4C) and left end view (4D).
Figure 4B:
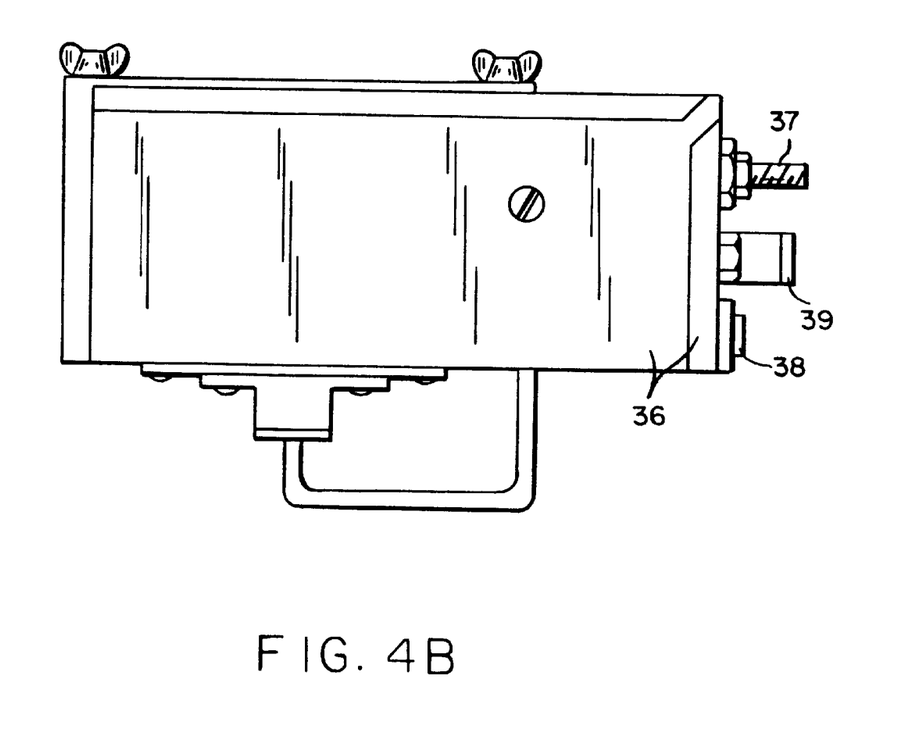
Figure 4C:
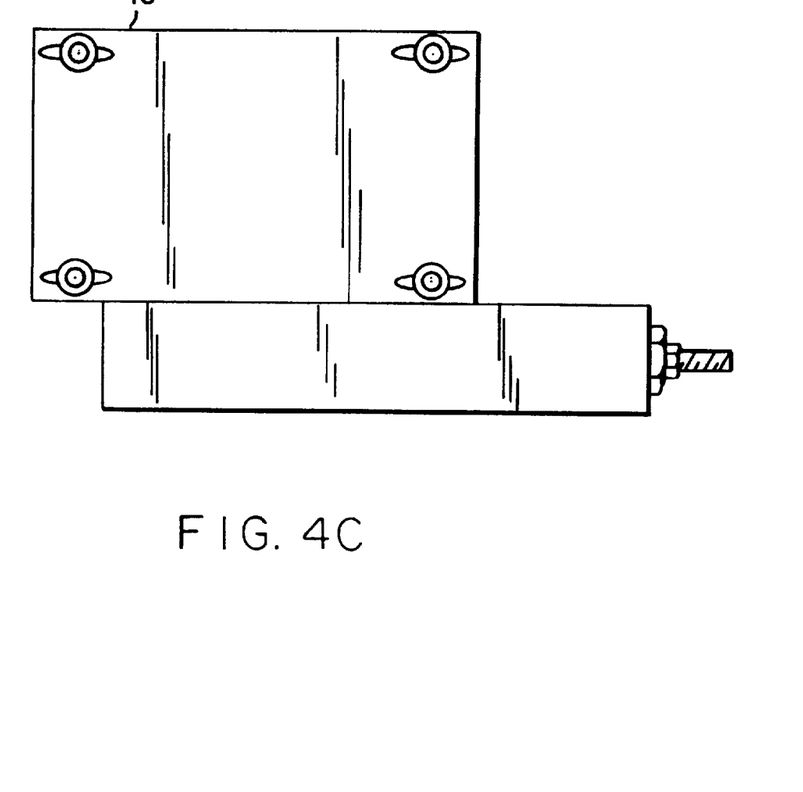
Figure 4D:
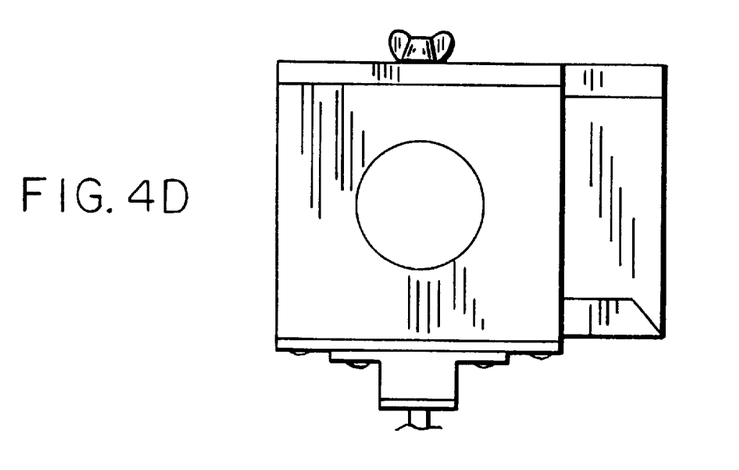

The in-line viscometer of the present invention combines the concept of a "falling member" with a compact bi-directional flow concept and an easily opened and cleaned measuring chamber. It is also very compact in size and does not require a specific flow of fluid to operate. Another advantage of this invention is the fact that fluid can flow in either direction through the chamber—a benefit for installing on opposite sides of a press.

As described above, the viscometer of the present invention comprises a chamber, and inside the chamber is secured a measuring tube and a falling piston. The piston has a lift plate secured to its top by means of a short small shaft—advantageously this is a one-piece unit. There are one or more lifting fingers, which operate through a defined distance large enough to raise the piston up and then drop back down to a base position thus leaving the piston free to fall by gravity to its lowermost position. However, the mechanical design is such that these fingers when lowered will not touch the actual piston itself. Mounted underneath the piston, when it is in its lowermost position, is a proximity switch that is used to sense when the piston is in its lowermost position. The time it takes to travel from its raised position to its lowermost position is a unction of viscosity.

An external controller as discussed in greater detail below is preferably used to cycle this measuring element and measure the piston time of fall. Alternately a generic programmable controller can be used to operate this device. The Prior Art Type 1 and 2 and Type 4 devices can be difficult and in some cases impossible to operate directly with a programmable controller.

The Figures accompanying this specification describe in detail the preferred embodiment of this invention. As illustrated therein, the original prototype was built from a combination of Delrin™, stainless steel, Teflon® and aluminum. All wetted parts could be fabricated from any metal, or plastic, or epoxy, or other synthetic or natural materials, if the necessary rigidity and chemical compatibility to products being measured were maintained. Non-wetted parts can be made from many different materials, limited only by their ability to be formed, fabricated and durable.

The following specific comments are provided regarding the parts used to construct the preferred viscometer of the present invention, with reference specifically to the several Drawing Sheets accompanying this specification:

Reference No. 1 is a proximity switch clamp. Reference No. 1 holds the proximity, switch 34 in the proximity switch holder 2 by means of screws threading into 2. These screws are not shown in the drawings. Proximity switch holder 2 provides a location into which proximity switch 34 is placed with and end thickness sufficiently small enough so that proximity switch 34 can sense the presence of piston 28 and still provide pressure isolation of fluid within chamber 15 and the external atmosphere around the unit.

Reference No. 2 is a proximity switch holder. This is the one item that should be limited in its material of construction, preferably to a material that can allow the proximity switch 34 to sense the closeness of piston 28. The original design used a type of proximity switch that requires a non-metallic construction so that it could detect the metal content of the piston. There are other types of proximity switches that are available, for instance, those that can sense magnetic fields connecting 28 to 34. There also may be other types of non-contract measuring techniques that could be applied at this point.

Reference No. 3 is a proximity switch gasket that provides a fluid seal. This gasket could also be used in position 45. Reference No. 4 is the measuring tube assembly, which is typically made from stainless steel (SS). It can be made from one single piece or from several pieces pressed together. The bore clearance between 28 and 29 defines much of the measuring range of the unit and the slot therein is used to allow good sampling. The slot should be at right angles to the flow of product so that there is no impingement of flow against the piston, which might cause the piston to drag against the side of the tube.

Reference No. 5 is an air cylinder coupling. This coupling screws onto the end of the shaft of air cylinder 14 and provides a place to insert the air cylinder coupling pin 6. The hole through coupling 5 must be large enough so that pin 6 does not cause binding to occur between the lifting shaft connector rod 7 and the air cylinder shaft 17, as the air cylinder strokes in and out.

As illustrated, pin 6 has retainers on both ends. This provides a means of joining the air cylinder coupling 5 and the lifting shaft connector rod 7 together. Later modifications include a new design that has a pin that is spring loaded. Reference No. 7 is a shaft that is pressed into lifting shaft 23. It provides a firm connection between the air cylinder 14 and lifting shaft 23.

Reference No. 8 is a packing plate that is used to hold shaft packing 19 in its required position. Packing plate 8 also provides some guidance to lifting shaft 23 which when coupled with lifting shaft end bearing 22 and shaft packing 19 give good support to the lifting shaft 23. This plate 8 also provides some compression to the packing 19. Plate 8 is designed to squeeze the packing and thus insure a good seal around the lifting shaft 23.

Reference No. 9 is the chamber cover, which can be constructed of solid metal, colored plastic or clear plastic or combination thereof. Some models of this invention have used opaque Delrin and Teflon covers, but other cover materials could likewise be used; for example, metal, clear plastic, opaque plastic or translucent plastic. The cover 9 could also be a metal provided with a plastic or glass window. The cover 9 can have an extended portion, into the chamber, shown as 46. This would be useful with very low flows that might not have sufficient velocity to flush out any air at the top of the chamber, shown as Reference No. 43. This extensions eliminates places where air can remain, especially if the first process connector 18 and/or the second process connector 25 are raised up toward cover 9.

Reference No. 10 is a set of cover fasteners, which can take any number of configurations. For example, they can be studs fastened into chamber 15 onto which nuts or wingnuts are placed. In the latest cover design, four corner bolts are used to secure a stainless steel plate on top of the cover. Added to the middle of the plate is a bolt that can be tightened down (through the stainless steel plate) thus applying tremendous force against the cover to prevent leakage. Such a sealing addition has provided up to 60-psi pressure without leakage. Alternately the threaded rod can be integral to the wingnut with a tapped hole in chamber 15. Alternately fastener 10 can be made oversized and hang over the edge of chamber 15 in various places so that cover 9 can be secured by a swing bolt 47. This would allow one to have the bolts permanently fastened to chamber 15 and would also eliminate the possibilities of stripping threads in chamber 15.

Reference No. 11 is a cover gasket made from a material suitable for the liquid materials being measured. Reference No. 12 is a lifting air supply, from a remote valve (not shown). This remote valve could be a single four-way air valve or possibly two different three way valves. In the preferred embodiments, four way valves are employed. When one side turns on, the other must exhaust at once—otherwise a time delay occurs, which can lead to erratic readings. When air pressure is applied to the lifting air supply 12 and the measuring air supply 13 is vented, the air cylinder 14 will retract the air cylinder shaft 17. This causes the lifting shaft 23 to rotate counterclockwise and the lifting pin 21 will lift piston 28. Air cylinders are available with numerous different mounting and types of air connections, none of which are believed to be critical herein.

Reference No. 13 is a measuring air supply from a remote valve (not shown). If desired, one could use a spring return air cylinder, and thus one would need only a three-way air valve. When air is applied to the measuring air supply 13 and lifting air supply 12 is vented, the air cylinder 14 extends the air cylinder shaft 17, thereby causing the lifting shaft 23 to rotate clockwise, causing the lifting pin 21 to drop. This leaves the piston assembly 27 free to fall. When the piston assembly 27 falls close enough to the proximity switch holder 2 then the proximity switch 34 will detect its presence. The time between when air is applied to 13 and when 34 detects 27 is a measure of the viscosity of the test fluid.

Reference No. 14 is the air cylinder used to rotate lifting shaft 23. Alternates to this unit could be electric solenoid with different length of the lifting shaft connector rod 7 to account for reduced travel of air cylinder shaft 17. Also one could use a cylinder operated by hydraulic fluid or some other device to cause this motion.

Reference No. 15 is the basic chamber constructed of any material(s) suitable for fluids being measured. Chamber 15 can be made in various sizes. Reference No. 16 is the measuring tube assembly gasket used to prevent leakage of material from inside chamber 15. Such a gasket could also be placed at Reference location 48. Reference No. 17 is an air cylinder shaft. Reference No. 18 is the first process connection. This can be a pipe thread directly machined into chamber 15. Alternately it could be metal plate that is secured to chamber 15 and available with different connections such as welded nipple or a flange or some other type of connection device.

Reference No. 19 is Teflon shaft packing in the preferred design. Chevrons are compressed by packing plate 8 thus sealing around lifting shaft 23. Alternate materials include Viton™, Buna™, TFE equivalent; Grafoil™ or even airs seals depending upon the fluids being measured and the level of maintenance deemed acceptable to the end user of this equipment.

Reference No. 20 is a lifting rod, pressed into lifting shaft 23, used to convert rotation of lifting shaft 23 into near vertical motion. Reference No. 21 shows lifting pins pressed into lifting rod 20. Lifting rod 20 reaches in under piston lift plate 30 and thus can lift piston 28. Reference No. 22 is a hole or pressed in bearing for the end of lifting shaft 23. This along with shaft packing 19 and packing plate 8 provide a secure and stable set of guides for lifting shaft 23. Lifting shaft 23 is used to connect air cylinder 14 to the piston assembly 27.

Reference No. 24 shows the flowpath of the fluid as it passes in and out from under the piston 28, along the side of the piston 28 and out the slots on either side of the measuring tube 4. Reference No. 25 shows the second process connection. If this point is at the opposite end from the first process connection 18 then the chamber is "reversible" meaning fluid flow may pass through the chamber 15 in either direction.

There are numerous brackets available to secure the air cylinder 14 to chamber 15. Reference No. 26 is an air cylinder support bracket, which is bolted to chamber 15 and then the cylinder mounts to the bracket by means of a nut and threaded end.

Reference No. 27 is the piston assembly, which is comprised of three parts 28, 29, and 30, all permanently fastened to each other by conventional machining techniques such as press fit or pinning, or single piece machining. Reference No. 28 is the piston, Reference No. 29 is a piston extension rod and Reference No. 30 is the piston lift plate.

Reference No. 29 is used to connect piston 28 and piston lift plate 30. It has been discovered that the outer diameter of lift plate 30 is very critical. The outer diameter of piston lift plate 30 must be larger than the actual piston in order to prevent the piston 28 from wobbling –0.735 in. has been found to be a good number. When using a small OD on the main piston body [such as 0.725 in.], it falls into the bushing giving erratic readings. If the outer diameter of lift plate 30 is smaller than the piston itself, the unit will not be sufficiently repeatable. If one were to use an OD of 0.745 in., that would leave the cap at 0.735 in. since the main body of the piston 28 is so large that the wobble factor dissipates. Future experimentation may permit changes in the 0.735 dimension.

In the currently preferred embodiment machining a solid rod of stainless steel forms the piston 27. It had been determined that using separate pieces caused variances of just a few thousandths of an inch in concentricity and this could result in erratic readings. Reference No. 28 shows the basic piston ranges in diameters from 0.600 to 0.749 inches with a length of approximately 1-inch. This can be designed in a very small size, for example 0.25 inches if needed to reduce overall size of system. The bore in the proximity switch holder 2 would also decrease in size, as would all other dimensions of the proximity switch holder 2.

Reference No. 30 illustrates the piston lift plate which lifting pin 21 will push up against to lift the piston assembly 27. (Note—there is no Reference No. 31). Reference No. 32 illustrates an alternate piston lift pin, which is pressed through piston extension rod 29 and lifting pins 21 are removed. Thus the lifting rod 20 is lifted on piston lift pin 32, thereby lifting the piston assembly 27. This scheme makes it much easier to remove the piston 28 from the proximity switch holder 2 when cover 9 is removed. The use of piston lift plate 30 and lifting pin 21 require disconnecting lifting shaft connector rod 7 from the air cylinder coupling 5 to remove the piston assembly 27.

Reference No. 33 represents two slots on each side of the proximity switch holder 2. These slots are used to provide a sample of fluid for drawing in and out along pathway 24. Reference No. 34 illustrates a proximity switch, but could also be magnetically sensitive switch that would thus allow the proximity switch holder 2 to be constructed from all metal.

Reference No. 35 is a drain tube, which serves as an alternate flow path to the second process connection 25. If external mounting requirements and/or available flow rate prevent the use of the second process connection 25 then chamber 15 could be designed with drain tube 35 and a connection at bottom of the drain tube 35 could be used to return fluid to some point desired by the user. Also it would be possible to change the first process connection 18 into something like drain tube 35 but probably of a shorter length. This would allow fluid connections of both inlet and outlet to be made from under the entire unit.

Reference No. 36 shows a sheet metal housing use to protect the various components of the system as well as provide mounting surface for proximity switch connector 37 and measuring air supply connector 39. The housing 36 is typically constructed of two pieces but it could be made from one or more pieces.

Reference No. 37 shows an electrical proximity switch connector of a design compatible with proximity switch 34 and suitable for use in the environment where the unit will be used. There could be instances where users want to directly wire the switch and thus this item might not be always be used.

Reference No. 39 illustrates the lifting air supply connection whereby air is supplied to lift the piston assembly 27. This is mounted into housing 36 and internally connected to air cylinder 14 by means of air tubing and appropriate fittings. Reference No. 38 shows the measuring air supply connection mounted directly into the end of cylinder 14, and protruding through housing 36. Air cylinders come in many different designs and thus it is possible that this could also be mounted in housing 36 and connected to chamber 15 by means of tubing and fittings. Reference Nos. 12 and 13 represent the lifting air supply and the measuring air supply respectively.

Reference No. 40 shows alternate locations of mounting bolts that would be required if the process connections 18 or 25 were required to be nearer to cover 9.

Reference No. 41 shows an alternate internal design (rounded corners) for the elimination of pockets and to make the unit more effective for flushing, i.e., for inline cleaning and/or volume reduction.

Reference No. 42 shows another alternate internal design (rounded sides) for the elimination of pockets and to make the unit more effective for flushing, i.e., for inline cleaning and/or volume reduction. This modification could be used in conjunction with design modification 41.

Reference No. 43 shows a top fluid zone, which in low flow installations might not purge and thus cover extension 46, could be used along with design modification 42 to prevent this problem.

Reference No. 44 shows a bottom fluid zone, which in low flows might not flush well. Accordingly, the rounded corner design modification 41 would be used to prevent this problem.

Reference No. 45 is an alternate gasket location to 3. Reference No. 46 shows an extended cover that extends down into 15 in order to minimize or eliminate 43. Reference No. 47 is cover swing bolt, which could be used as an alternative to replace cover bolt 10. The swing bolt 47 provides easy loosening and then swings free of cover 9. Reference No. 48 is an alternate gasket location to 16 for the measuring tube assembly gasket.

As illustrated, the in-line viscometer of the present invention combines the simple concept of a "falling member" viscometer with a compact bidirectional flow concept, in a simple unit that is easily opened and cleaned. In its most preferred embodiment, the unit is very compact in size and does not require a specific flow of fluid to operate. The preferred unit design also overcomes the limited life of a linear packing holder by advantageously using a mere 22 degrees of rotation with a positive operation by a cylinder. These features are important for several reasons, including:

1. There is a trend in some printing applications to the use of low flow pumps and thus there is insufficient ink available to both operate the viscometer and feed the process. This unit can be mounted directly in the fluid line between the pump and the process.
2. During some pumping operations, the pump may cause a "pressure" surge that can adversely impact the performance of devices using flow to lift the piston.
3. There is a growing trend in ink pumping of requiring "speedy" changeovers between jobs and this requires equipment, which is both more compact and easier to open and clean.
4. The growing emphasis on quick changes and ease of installation make the bidirectional flow nature of this device of great value. This is also an inherent value making it less likely that an installation will be made incorrectly.
5. There is yet another benefit of bi-directional flow. Some inking systems have recently been developed that pump ink through the line to the process. When the process is done they suck the ink back through the line. Then they may flush the lines in either direction. During such evacuation and flushing the viscosity unit of this invention can continue to operate and keep the space clean beneath the piston. The process operators do not need to open any special valves to allow this unit to be flushed. The customer just does his normal action and the unit responds accordingly.

6. This new invention uses a Teflon seal but in a partial rotational form. A shaft passes through the Teflon but only rotates on a small angle. This distinction over the prior art prevents ink particles from being drawn into the seal packing, preventing premature wear.

In the preferred embodiment, an externally mounted air cylinder with a known stroke distance controls the distance these fingers travel. An external air valve controls this cylinder. The connection between the air cylinder and the lifting fingers are a very important and new feature of this device. Instead of using a linear acting rod through Teflon packing the preferred unit of this invention uses a "partial rotational". The air cylinder cycles in and out and is connected to an arm, which in turn connects to a shaft, which rotates just 22 degrees through Teflon packing. The 22-degree rotation is preferred for one embodiment of this invention. Depending upon the size of the unit components, and other considerations, angles greater than or less than 22 degrees could be used. Using the Teflon packing in this manner makes the pressure setting on the packing less critical. The top of the chamber can be removed with the simple loosening of some captive bolts, which are used to secure the cover on the chamber.

The ability to work on high, low and no flow conditions bi-directionally while at the same time having a drastically improved life on the packing combine to make this a very advantageous advance in the measuring of viscosity in-line.

In addition, by merely adding solvent into the chamber, for instance, when additions are being made to correct viscosity, or when there is a flushing operation in a process, will clean the viscometer of the present invention. When a flushing operation is underway the unit of this invention could simply be used to measure the viscosity of the flushing fluid. The flushing fluid would also clean under the piston during the flushing process.

The preferred design of the unit also overcomes the limited life of a linear packing holder. The lifting of the piston is accomplished by means of an externally mounted air cylinder. The air cylinder has its shaft extended and retracted by means of a connection to a lever. This lever causes a shaft, passing through a packing to the inside of the measuring chamber, to rotate through a fixed distance, whose other end is connected to another lever used to lift the piston a fixed distance.

While use of packing for the rotation shaft to go through is preferred, other concepts could be substituted without adverse impact on the operation of the unit. For example, a lever attached to a flexible diaphragm that levitates the piston directly, like a seesaw, could be used rather then using rotational motion to obtain vertical motion. When the air cylinder is in its extended position the lifting member will be in a lower most position, allowing the piston to fall. When in its retracted position the piston will be lifted to it's raised position. A proximity switch is mounted in a vertical orientation, under the piston, separated from the process fluid by a plastic or other type of seal. When the metal piston falls to the bottom of its measuring tube the proximity switch will be operated.

The viscometer of the present invention has been designed for use on both water based and solvent based fluids with wetted parts being constructed of appropriate materials. The working viscosity range for this device is estimated to be from less than 1 centipoise to approximately 1,000 centipoise. Pressures are primarily low, limited primarily by the seal between the proximity switch under the piston. Teflon packing can be substituted with a number of other packing materials if the process fluid being measured is not compatible with Teflon. An electrical, steam or hydraulically operated device could be used in place of the air cylinder. The size of the chamber can be made of varying sizes and the inlet/outlet connections can be through the bottom or top of the chamber in lieu of the end connections, as shown in the drawings.

While the illustrated embodiment shows the inlet and outlets being at the same elevation, it may be advantageous to have the inlet lower than the outlet. This lets the unit drain out during the evacuation phase. Accordingly, it is believed that the skilled artisan can readily determine which type of inlet/outlet connection is best suited for particular operations and all such connections are contemplated as being part of this invention. For example, even top and bottom connections can be used if desired.

In the preferred embodiment, the typical size of the measuring tube is 0.750 inches and its length is suitable to provide protection for the piston. The lift used in this unit is ½" though the design can easily be adjusted to work with different lifts. The slots are provided for sampling and can be varied in length, as can the diameter of the piston and/or bushing to achieve different times of fall for different viscosities.

It is possible to secure the lifting fingers to the piston and thus "drive" it both up and down. This would be used for very high viscosities. The idea of driving the piston both ways is covered by our prior patent for the M20. It is the use of the partially rotating shaft that is one of the key new ideas in this invention.

The present invention has been described in detail, including the preferred embodiments thereof However, it will be appreciated that those skilled in the art, upon consideration of the present disclosure, may make modifications and/or improvements on this invention and still be within the scope and spirit of this invention as set forth in the following claims.

What is claimed is:

1. A viscometer, designed to be connected to a fluid flow stream, either directly or indirectly, for measurement of the viscosity of the fluid in said flow stream, said viscometer comprising:

(a) a sealed chamber having a fluid inlet and a fluid outlet, said chamber serving as an in-line housing for conducting continuous measurements of the viscosity of liquids passing therethrough;

(b) a measuring tube and a falling piston inside said measuring tube, the combination thereof being mounted inside said chamber, and wherein the piston has a lift plate secured to its top by means of a shaft;

(c) lifting fingers in contact with said piston, said fingers defining the distance between the upper piston limit and the lower piston limit; but leaving said piston free to fall by gravity to its lowermost position;

(d) a proximity switch mounted proximate to the piston, said proximity switch used to sense when the piston has reached its lowermost position;

whereby the measured time taken for the piston to travel from its upper piston limit position to its lowermost position is a direct function of the viscosity of the liquid in the chamber.

2. The viscometer of claim 1, further comprising an external controller means to measure the piston time of fall.

3. The viscometer of claim 1, further comprising a programmable controller means to measure piston time of fall.

4. The viscometer of claim 1, wherein the distance the fingers travel is controlled by an externally mounted air cylinder with a known stroke distance, said air cylinder further comprising a reciprocating piston mechanism.

5. The viscometer of claim 4, wherein the air cylinder is controlled by an external air valve.

6. The viscometer of claim 5, wherein the connection between the air cylinder and the lifting arms relies upon a rotational relationship, whereby the air cylinder cycles in and out and is connected to the lifting arm which in turn connects to a shaft which rotates under about 30 degrees.

7. The viscometer of claim 6, wherein the rotation is less than about 25 degrees.

8. The viscometer of claim 6, wherein the rotation is about 22 degrees.

9. The viscometer of claim 1 furthers comprising a removable top.

10. The viscometer of claim 1, wherein the measurable viscosity ranges for the viscous fluids is from less than about 1 centipoise to about 1000 centipoise.

11. The viscometer of claim 10, wherein the viscous fluid is selected from water based and solvent based fluids.

12. The viscometer of claim 1, wherein the inlet and outlet connections are both through the bottom of the chamber.

13. The viscometer of claim 1, wherein the inlet and outlet connections are both through the top of the chamber.

14. The viscometer of claim 1, wherein the inlet and outlet connections are at opposite ends of the chamber.

15. The viscometer of claim 12, 13, or 14, wherein the inlet and outlet connections are staggered.

16. The viscometer of claim 1, wherein the lifting fingers the piston to be driven upwardly.

17. The viscometer of claim 1, further comprising both the partially rotating/reciprocal shaft with lifting fingers for moving the piston and an external air cylinder to do the movement in a positive and absolute manner.

18. The viscometer of claim 1, wherein the piston includes a mechanical extension such that when the lifting fingers are raised the piston will raise and when they are lowered they do not produce any downward force on the piston but allow it to fall by means of gravity.

19. The viscometer of claim 1, wherein the proximity switch is mounted horizontal to the piston assembly.

20. The viscometer of claim 1, wherein the proximity switch is mounted at the bottom of the piston assembly.

* * * * *